United States Patent [19]

Martan et al.

[11] 4,038,325

[45] July 26, 1977

[54] ISOMERIZATION OF CIS-ANETHOLE TO TRANS-ANETHOLE

[75] Inventors: Michael Martan, Skokie; Paul H. Reichenbacher, Schaumburg, both of Ill.

[73] Assignee: UOP Inc., Des Plaines, Ill.

[21] Appl. No.: 625,290

[22] Filed: Oct. 23, 1975

[51] Int. Cl.² ............................................. C07C 41/00
[52] U.S. Cl. ................................................. 260/612 D
[58] Field of Search ................................... 260/612 D

[56] References Cited

PUBLICATIONS

Bergman, Isomerism and Isomerization (1948), pp. 27–31.

Cramer, J.A.C.S. vol. 88 (1966), pp. 2272–2276.

*Primary Examiner*—Bernard Helfin
*Attorney, Agent, or Firm*—James R. Hoatson, Jr.; Raymond H. Nelson; William H. Page, II

[57] ABSTRACT

Cis-anethole is isomerized to the trans-anethole form thereof by treatment with a rhodium-containing compound such as rhodium chloride in an alcoholic medium at the reflux temperature of said medium to form the desired trans isomer.

4 Claims, No Drawings

ISOMERIZATION OF CIS-ANETHOLE TO TRANS-ANETHOLE

BACKGROUND OF THE INVENTION

Anethole which is also known as p-methoxypropenylbenzene or p-propenylanisole is employed in many fields in industry. For example, it is the starting material for the manufacture or synthesis of anisic aldehyde. Likewise, it is also used in color photography; as a sensitizer in color bleaching processes; in perfumes, particularly as an additive to toothpastes as well as to cosmetic preparations; as a flavor for liqueurs and as a flavor for licorice candies. Most of the anethole which is used in this respect is extracted from natural sources, it being a main component of many essential oils such as pine oil, anise oil, fennel anise star oil, or in anise seed. However, the natural sources are subject to varying conditions in nature and therefore shortages of the natural sources may develop during a period of time. In order to overcome those shortages and not be dependent upon a natural crop, some routes for the synthetic preparation of anethole have been developed.

However, the drawback or disadvantage which is present in these syntheses of anethole is that said syntheses result in a mixture of the cis and trans isomers. Additionally, anethole obtained from certain natural sources is a mixture of cis and trans isomers. Inasmuch as the edible isomer is the trans form of anethole and in cosmetic and food stuffs an admixture of more than 1% of the cis isomer cannot be tolerated due to the toxicity of the cis isomer and the fact that said isomer possesses a sharp, unpleasant taste, it is necessary to isomerize or separate the cis isomer from the trans isomer. The separation of the cis isomeric form of anethole from the trans isomeric form is difficult to accomplish due to the fact that the two isomers possess relatively similar boiling points. Therefore, an isomerization process is required in which the cis isomer is converted to the trans isomer in substantially quantitative amounts, that is, above about 90% in order that a fractional distillation may be effected to separate the remaining cis isomeric form of anethole from the trans isomeric form. As will hereinafter be shown in greater detail, we have now discovered that by utilizing certain catalytic compositions of matter it is possible to effect an isomerization process whereby substantially all of the cis isomer of anethole which is present in an admixture of cis- and trans-anethole is converted to the trans isomer.

This invention relates to an isomerization process for the conversion of cis-anethole. More specifically, the invention is concerned with a process for the treatment of an admixture of cis-anethole and trans-anethole whereby the cis form is substantially isomerized to the trans form thereof in the presence of certain catalytic compositions of matter.

As was hereinbefore set forth, it is necessary, in order to utilize anethole as a flavoring agent in cosmetics such as toothpaste and in food stuff to provide a licorice flavor to the food stuff, that the anethole be present in the trans isomeric form thereof. By utilizing certain catalytic compositions of matter of a type hereinafter set forth in greater detail, it has been found to be possible to effect such an isomerization of the cis form of anethole to the trans form thereof.

It is therefore an object of this invention to provide a process for the isomerization of cis-anethole.

A further object of this invention is to provide a process for the obtention of relatively pure trans-anethole from a mixture of cis-anethole and trans-anethole by subjecting said mixture to an isomerization process utilizing rhodium-containing catalysts.

In one aspect an embodiment of this invention resides in a process for the isomerization of cis-anethole which comprises treating cis-anethole with a rhodium-containing compound in an alcoholic medium at isomerization conditions, and recovering the resultant isomerized anethole.

A specific embodiment of this invention is found in a process for the isomerization of cis-anethole which comprises treating a mixture of cis- and trans-anethole with rhodium chloride in an absolute ethanol medium at a temperature in the range of from about 25° to about 200° C. and a pressure in the range of from about 25° to about 200° C. and a pressure in the range of from about atmospheric to about 100 atmospheres and recovering the resultant isomerized anethole.

Other objects and embodiments will be found in the following further detailed description of the present invention.

As hereinbefore set forth the present invention is concerned with a process for the isomerization of cis-anethole to trans-anethole. The isomerization is effected by treating cis-anethole or a mixture of cis- and trans-anethole with a rhodium-containing compound in an alcoholic medium. The isomerization of the cis-anethole to the trans form thereof by utilizing a rhodium-containing compound was totally unexpected in view of the fact that isomerization catalysts which may be utilized for the isomerization of similar systems such as allylbenzene were ineffective as isomerization catalysts in the treatment of cis-anethole. For example, as will hereinafter be shown in greater detail, cobalt carbonyls, iron carbonyls or heterogeneous catalyst systems such as palladium on charcoal, platinum on charcoal, etc., when used at relatively low temperatures in order to increase the formation of the trans isomer did not work.

The desired isomerization of cis-anethole to trans-anethole is effected in an alcoholic medium at temperatures ranging from about 25° up to about 200° C. or more and at pressures which may range from about atmospheric to about 100 atmospheres. In the preferred embodiment of the invention the reaction temperature will be the reflux temperature of the particular alcohol which is used as the isomerization medium. However, it is also contemplated within the scope of this invention that when superatmospheric pressures are afforded by the introduction of a substantially inert gas such as nitrogen, argon, helium, etc., into the system are employed, it is possible to utilize temperatures greater than the reflux temperature of the alcohol. Examples of alcohols which are employed as the medium for the isomerization reaction will include those aliphatic alcohols containing from 1 to about 9 carbon atoms such as methyl alcohol, ethyl alcohol, n-propyl alcohol, isopropyl alcohol, n-butyl alcohol, sec-butyl alcohol, isobutyl alcohol, t-butyl alcohol, n-amyl alcohol, 2-pentanol, 3-pentanol, 2-methyl-1-butanol, 3-methyl-2-butanol, isoamyl alcohol, t-amyl alcohol, neopentyl alcohol, the isomeric hexyl, heptyl, octyl and nonyl alcohols.

Examples of rhodium-containing compounds which are utilized as isomerization catalysts for the process of this invention will comprise both inorganic and organic salts of rhodium such as rhodium chloride, rhodium bromide, rhodium iodide, rhodium nitrate, rhodium sulfate, rhodium formate, rhodium acetate, rhodium propionate, rhodium butyrate, rhodium acetylacetonate, etc. It is to be understood that the aforementioned rhodium-containing compounds are only representative of the class of compounds which may be employed, and that the present invention is not necessarily limited thereto.

The isomerization process of the present invention in which the cis-anethole is converted to trans-anethole may be effected in any suitable manner and may comprise either a batch or continuous type operation. For example, when a batch type operation is to be used, a quantity of the cis-anethole or the mixture of cis-anethole and trans-anethole is placed in an appropriate apparatus along with the rhodium-containing compound and a desired amount of the alcoholic medium, which in the preferred embodiment of the invention is in the absolute state. If the reaction is to be effected at atmospheric pressure, the reaction vessel may comprise a flask which is provided with heating and refluxing means. Alternatively, if the reaction is to be effected utilizing superatmospheric pressure, the appropriate reaction vessel will comprise an autoclave of the stirring or mixing variety. The reaction mixture is then heated to the desired reaction temperature which, as hereinbefore set forth, preferably comprises the reflux temperature of the particular alcohol which is used as the reaction medium and maintained thereat for a predetermined period of time which may range from about 0.5 to about 10 hours or more. At the end of the reaction time, heating is discontined and the reaction mixture is recovered. When utilizing an atmospheric pressure for the reaction, the alcoholic medium may be stripped from the anethole at the end of the reaction period by disconnecting the reflux condenser. Thereafter the bottoms from the reaction are subjected to fractional distillation whereby the desired trans-anethole is separated from any unreacted cis-anethole which still may be present, the latter then being subjected to further isomerization in a second reaction step.

When utilizing superatmospheric pressures and effecting the reaction in a pressure-resistant vessel such as an autoclave, a similar procedure may be followed in order to recover the desired product. For example, when superatmospheric pressures are employed, heating is discontinued at the end of the predetermined residence time for the reaction and the apparatus is allowed to return to room temperature. Upon returning to room temperature, the excess pressure which has been afforded by the introduction of a substantially inert gas such as nitrogen into the pressure vessel is released, the autoclave is opened and the mixture is recovered therefrom. The alcoholic medium may be separated from the bottoms by distillation following which the bottoms are then subjected to fractional distillation to separate the trans-anethole from the cis-anethole.

When utilizing a continuous manner of operation for the isomerization of cis-anethole to trans-anethole, the starting material is continuously charged to a reaction vessel which is maintained at the proper operating conditions of temperature and pressure. In addition, the mixture of the alcoholic medium and the rhodium-containing compound is also charged to this reactor through a separate stream. The reactor effluent, after passage of a predetermined residence time, is continuously withdrawn and subjected to separation steps such as distillation whereby the alcoholic medium is separated from the isomerized anethole, the latter being then further charged to a fractionation column for separation of any unreacted cis-anethole from the trans-anethole, the former along with the alcohol being recycled to the reaction zone to form a portion of the feed stock. Likewise, the rhodium-containing compound may also be recovered and subjected to treatment whereby the rhodium portion of the compound may be recovered for further use.

The following examples are given for purposes of illustrating the isomerization reaction of the present invention utilizing a rhodium-containing compound. However, it is to be understood that these examples are given merely for purposes of illustration and that the present invention is not necessarily limmited thereto.

EXAMPLE I

In this example 100 grams of anethole having a cis/trans composition of 25:75 were mixed with 20 milligrams of rhodium trichloride containing 40% rhodium and 50 ml of absolute ethyl alcohol in a reaction vessel provided with heating and refluxing means. After purging the flask with nitrogen, the reaction mixture was heated to about 75° C. and refluxed for a period of 8 hours. At the end of this period, analysis by means of gas-liquid chromatography disclosed that the cis/trans composition of the anethole had changed to 5% cis and 95% trans. The reflux condenser was then disconnected and the absolute ethyl alcohol was stripped from the reaction mixture. After completion of the stripping of the ethyl alcohol, 50 milliliters of the bottoms were subjected to fractional distillation under a reduced pressure of 30 mm of mercury. Each 5 milliliter fraction of the bottoms was collected at a rate of 2 milliliters per hour and subjected to gas-liquid chromatographic analysis. The analysis of the fractions is summarized in the following table.

TABLE I

| | Fractionation of Isomerized Anethole | | |
|---|---|---|---|
| Cut | Temp. | Light Components | Cis | Trans |
| 1 | 119.0 | 67.0 | 25.8 | 7.2 |
| 2 | 124.5 | 6.2 | 27.0 | 66.8 |
| 3 | 124.5 | — | 7.3 | 92.7 |
| 4 | 127.0 | — | 4.8 | 95.2 |
| 5 | 127.0 | — | 2.0 | 98.0 |
| 6 | 127.0 | — | 0.7 | 99.3 |
| 7 | 127.0 | — | — | 100.0 |
| 8 | 127.0 | — | — | 100.0 |
| 9 | 127.0 | — | — | 100.0 |

In addition, another step which was performed prior to stripping ethyl alcohol was to allow the solution to cool to room temperature and treat said solution with alumina in a weight ratio of 10 grams of anethole to 2 grams of alumina. The rhodium precipitated and was separated by decantation. Analysis of the precipitate showed that 98% of the rhodium was recovered in said precipitate.

When the above experiment was repeated using 40 milligrams of rhodium trichloride per 100 grams of anethole in an absolute ethyl alcohol medium, the conversion of the cis/trans-anethole mixture in which the composition was 25:75 cis/trans to a cis/trans composition of 5:95 was accomplished in a period of 1 hour. Again fractional distillation under reduced pressure permitted the separation of the 5% cis from the mixture thus permitting the recovery of all of the trans-anethole. In addition, the rhodium was recovered from the bottoms distillation in a yield of 97%.

EXAMPLE II

To illustrate the unexpected results which were obtained when utilizing a rhodium-containing catalyst, an attempt was made to subject a cis/trans-anethole mixture utilizing cobalt acetylacetonate as an isomerization catalyst. Therefore, 2.0 grams of anethole along with 20 milligrams of lithium aluminum hydride and 10 milligrams of cobalt acetylacetonate were placed in a reactor which was then purged with nitrogen. The starting composition contained 38.9% cis-anethole and 61.1% trans-anethole. The reaction mixture was allowed to stand at room temperature for a period of 18 hours, at the end of which time no isomerization of the cis-anethole to trans-anethole had taken place.

EXAMPLE III

In a manner similar to that set forth in Example II above 2.0 grams of anethole, 2.0 grams of absolute ethyl alcohol and 2.36 milligrams of dicobalt octacarbonyl were placed in a reactor provided with heating means and reflux means. The starting composition of the anethole mixture consisted of 62.5% cis-anethole and 37.5% trans-anethole. After allowing the mixture to stand at room temperature for a period of 16 hours, analysis of the mixture disclosed that the composition of the anethole consisted of 63.4% cis isomer and 36.6% trans isomer. The mixture was then heated to a temperature of 55° C. and maintained in a range of from 55°-60° C. for a period of 3 hours. At the end of this 3-hour period, gas-liquid chromatographic analysis of the anethole disclosed the fact that the composition consisted of 58.1% cis isomer and 41.9% trans isomer, a relatively negligible amount of isomerization having occurred. After 16 hours of reaction while maintaining the temperature at about 60° C., the cis isomer dropped to 55% and the trans isomer increased to 45%. However, the amount of isomerization using dicobalt octacarbonyl as a catalyst was seen to be practically negligible.

EXAMPLE IV

As a further illustration of the unexpected activity of a rhodium-containing compound to act as an isomerization catalyst, another experiment was attempted in the isomerization of cis-anethole using triiron dodecacarbonyl as a catalyst. In this experiment 0.60 grams of an anethole mixture, 60 milligrams of triiron dodecacarbonyl and 1 cc of cyclohexane were refluxed under a nitrogen atmosphere at a temperature of 85° C. The anethole mixture which contained 37.7% cis isomer and 62.3% trans isomer at the beginning was analyzed at the end of 45 minutes, at which time it was found to contain 35.9% cis isomer and 64.1% trans isomer.

A repeat of this experiment using n-heptane as the medium and increasing the temperature to 100° C. resulted in reducing the cis isomer only to 32.6% at the end of 26 hours with a corresponding increase to 67.4% trans isomer. Again it is shown that the isomerization of the cis-anethole to trans-anethole using triiron dodecacarbonyl as a catalyst was negligible.

EXAMPLE V

In this example 100 grams of anethole which had a composition of 30/70 cis/trans isomers is mixed with 20 cc of absolute propanol and 40 milligrams of rhodium acetylacetonate. The mixture is heated to reflux (about 95° C.) and maintained thereat for a period of about 2 hours. At the end of this time, the reflux condenser is disconnected and the absolute propanol is stripped from the reaction mixture. The bottoms are subjected to analysis and will disclose that the cis/trans composition has isomerized to about 5:95. In a manner similar to that set forth in the above examples, this mixture is then subjected to fractional distillation under reduced pressure whereby the remaining cis isomer is removed and the entire amount of trans-anethole is recovered.

Similar results to that set forth above will also be obtained when utilizing other rhodium-containing compounds such as rhodium bromide, rhodium acetate or rhodium propionate as the catalytic agents for the isomerization process.

We claim as our invention:

1. A process for the isomerization of cis-anethole to trans-anethole which comprises treating cis-anethole with an inorganic or organic rhodium salt selected from the group consisting of rhodium chloride, rhodium bromide, rhodium iodide, rhodium nitrate, rhodium sulfate, rhodium formate, rhodium acetate, rhodium propionate, rhodium butyrate and rhodium acetylacetonate in an alcoholic medium at a temperature in the range of from about 25° C. to about 200° C. and a pressure in the range of from about atmospheric to about 100 atmospheres, and recovering the resultant isomerized anethole.

2. The process as set forth in claim 1 in which said alcoholic medium is methanol.

3. The process as set forth in claim 1 in which said alcoholic medium is ethanol.

4. The process as set forth in claim 1 in which said alcoholic medium is propanol.

* * * * *